United States Patent [19]

Tanaka et al.

[11] Patent Number: 4,556,517

[45] Date of Patent: Dec. 3, 1985

[54] CARBAPENEM DERIVATIVES

[75] Inventors: Kentaro Tanaka, Osaka; Naoki Tsuji, Hyogo, both of Japan

[73] Assignee: Shionogi & Co., Ltd., Osaka, Japan

[21] Appl. No.: 432,099

[22] Filed: Sep. 29, 1982

[30] Foreign Application Priority Data

Dec. 29, 1981 [JP] Japan .................................. 56-212435
Jan. 20, 1982 [JP] Japan .................................... 57-8144

[51] Int. Cl.[4] .................... C07D 487/04; A61K 31/40
[52] U.S. Cl. ............................................... 260/245.2 T
[58] Field of Search .................. 260/245.2 T; 424/274

[56] References Cited

U.S. PATENT DOCUMENTS 4,150,145  4/1979  Christensen et al. ........ 260/245.2 T
4,347,181  8/1982  Smale ........................... 260/245.2 T
4,473,578  9/1984  Corbett .............................. 424/274

OTHER PUBLICATIONS

Tsuji et al., Jour. of Antibiotics, vol. XXXV, No. 4, pp. 536–540, (1982).

*Primary Examiner*—Nicholas S. Rizzo
*Attorney, Agent, or Firm*—Wenderoth, Lind & Ponack

[57] ABSTRACT

A compound of the formula:

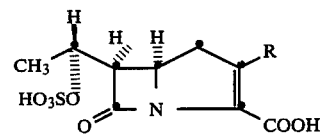

wherein R is carboxymethylthio, dihydroxymethylthio or hydroxymethylsulfinyl and the pharmaceutically acceptable salts being useful as a medicament and a veterinary drug for inhibiting the growth of gram-positive and gram-negative phathogenic microorganisms with β-lactamase inhibitory activity and a process for preparing the same.

3 Claims, No Drawings

CARBAPENEM DERIVATIVES

SUMMARY

A compound of the formula:

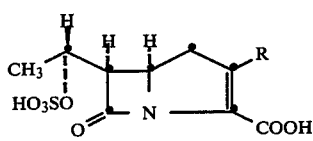

wherein R is carboxymethylthio, dihydroxymethylthio or hydroxymethylsulfinyl and the pharmaceutically acceptable salts being useful as a medicament and a veterinary drug for inhibiting the growth of gram-positive and gram-negative pathogenic microorganisms with β-lactamase inhibitory activity and a process for preparing the same.

This invention relates to new carbapenem derivatives and a process for preparing the same.

The carbapenem compounds of this invention are shown by the following formula:

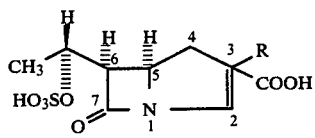

wherein R is carboxymethylthio, dihydroxymethylthio or hydroxymethylsulfinyl.

The said new compounds inhibit the growth of both gram-positive and gram-negative pathogenic microorganisms. Additionally, they show β-lactamase inhibitory activity against a wide range of β-lactamase producing organisms.

The compounds of the above formula are as follows. 3-Carboxymethylthio-6-(1-hydroxysulfonyloxyethyl)-7-oxo-1-azabicyclo[3.2.0]-hept-2-ene-2-carboxylic acid (referred to deoxy PLM B hereinafter), 3-dihydroxymethylthio-6-(1-hydroxysulfonyloxyethyl)-7-oxo-1-azabicyclo[3.2.0]-hept-2-ene-2-carboxylic acid (referred to deoxy PLM C hereinafter) and 3-hydroxymethylsulfinyl-6-(1-hydroxysulfonyloxyethyl)-7-oxo-1-azabicyclo[3.2.0]-hept-2-ene-2-carboxylic acid (referred to dihydro PLM C hereinafter).

Additionally, the group 3-dihydroxymethylthio of deoxy PLM C converts to formylthio under anhydrous condition. Both the formulae are referred to deoxy PLM C in this specification.

This invention includes the above three compounds as well as their pharmaceutically acceptable salts such as an alkali metal salts (e.g. sodium and potassium salt) and an alkaline earth metal salts (e.g. clacium and barium salt).

Many carbapenem antibiotics produced by actinomycetes such as having a group —CH(OSO₃H)—CH₃ at 6 position in formula I are known in references, for example, MM4550

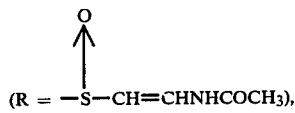

MM13902 (R=—S—CH=CHNHCOCH₃), MM17880 (R=—S—CH₂—CH₂—NHCOCH₃) and the like. The compounds of this invention have carboxymethylthio, dihydroxymethylthio or hydroxymethylsulfinyl as R in formula I. They are new compounds derived from the above known carbapenems, in which the 3-substituents R are of new sulfur-containing chain. Namely, these three compounds are new compounds.

Pluracidomycin A, B and C are antibiotics recently isolated from the fermentation broth of *Streptomyces pluracidomyceticus*(*J. Antibiotics* vol. 35, No. 4 pp 536–540 (1982)). The compounds of this invention can be prepared by reduction of pluracidomycin B and C (referred to PLM B and PLM C respectively hereinafter). Namely, deoxy PLM B may be produced by reduction of PLM B. Both deoxy PLM C and dihydro PLM C may be prepared by reduction of PLM C.

The physicochemical properties of these compounds are shown as follows:

TABLE 1

| Item | Deoxy PLM B | Deoxy PLM C | Dihydro PLM C |
|---|---|---|---|
| ¹H—NMRs spectrum (in D₂O, External Standard DSS) (J = Hz) δppm | 3.06 (1H, d-d, J = 10 and 18), 3.33 (1H, d-d, J = 9 and 18), 4.30 (1H, m), 3.84 (1H, d-d, J = 6 and 9), 4.80 1H, m), 1.49 (3H, d, J = 6), 3.49 (1H, d, J = 16), 3.60 (1H, d, J = 16) | 3.15 (1H, d-d, J = 10 and 18), 3.37 (1H, d-d, J = 9 and 18), 4.30 (1H, m), 3.84 (1H, d-d, J = 5 and 9), 4.80 (1H, m), 1.50 (3H, d, J = 6), 5.17 (1H, s) | 1.97 (3H, d, J = 6.5), 3.57 (1H, d-d, J = 10.5 and 18.5), 3.90 (1H, d-d, J = 9.5 and 18.5), 4.3~4.54 (3H, m), 4.95 (1H, m), 5.36 (1H, m) |
| Infrared absorption spectrum $\nu_{max}^{KBr}$ cm⁻¹ | 3440, 1750, 1595, 1390, 1255, 1225, 1170, 1070, 1040, 1020, 935, 900, 780, 690, 620, 580 | 3420, 1750, 1600, 1400, 1255, 1225, 1070, 1040, 1020, 935, 900, 780, 690, 620, 580 | 3430, 2930, 1770, 1620, 1590, 1400, 1250, 1230, 1065, 1020, 935, 895, 785, 625, 585 |

Note:
DSS = sodium 2,2-dimethyl-2-silapentane-5-sulfonate

The compounds of this invention are prepared as follows.

Deoxy PLM B and Deoxy PLM C are prepared from PLM B and PLM C respectively by removal of oxygen of the substituent at 2 position. The removal is effected by the usual methods such as reflux with triphenyl phosphine in tetrachloromethane, reduction with titanium trichloride, conversion to alkoxy-sulfonium salt followed by reduction with borohydride salt or borocyanate salt, reduction with chromous chloride (Y. Akita et al.: *Synthesis*, 1977, 792), reduction with phosphrus pentasulfide (I. W. J. Still et al.: *Synthesis*, 1977, 468), reduction with hydrogen sulfide and trifluroacetic anhydride (J. Drabowicz et al.: *Chem. Letters*, 1977, 767) and the like. Catalytic hydrogenation is not preferred since the sulfonyl group of the starting compounds is poisonous to catalyst and a large amount of catalyst is required. The reduction with titanium trichloride is most favorable for good yield and simple operation. The amount of titanium trichloride to be used is 4–9 eq. moles. The reagent is dissolved in a solvent from which the air dissolving is previously eliminated by suction under reduced pressure. The reaction is practised in nitrogen or carbon dioxide atmosphere. There are exemplified water, tetrahydrofuran, dioxane, diglyme and the like as a solvent. Reaction period is about 1 to 3 hours. It is preferred to keep the reaction pH at about 6–8.

Dihydro PLM C may be prepared by reduction with a reducing agent such as lithium borohydride, sodium borohydride, potassium borohydride and the like. Sodium borohydride is most favored. The reaction may be effected at room temperature for about 1 to 2 hours at about pH 6–8, prefarably 7 in water or a water miscible solvent such as alcohols (e.g. methanol and ethanol), tetrahydrofuran, dioxane and the like.

The starting compounds, PLM B and PLM C are disclosed in the *Journal of Antibiotics*, Vol. 35, pp 536–540 (1982) and prepared by cultivation of *Streptomyces pluracidomyceticus* PA-41746 in a suitable medium under aerobic condition. The strain, *St. pluracidomyceticus* PA-41746 has been deposited in Fermentation Research Institute at Tanidabe-cho, Tsukuba-gun, Ibaragi Prefecture in Japan since Apr. 17, 1981. The deposit was effected with accession number FERM-P 5964 at the begining and has been transferred to the condition under Budapest Treaty with accession number FERM-BP-174 since Sept. 6, 1982.

The production of PLM B and PLM C is effected by cultivating *St. pluracidomyceticus* PA-41746 in a suitable medium under aerobic condition and isolating the PLM B and PLM C from the fermentation broth. The composition of the culture medium and the conditions for the fermentation follow the generally known ones for producing antibiotics. The medium essentially consist of carbon sources, nitrogen sources and inorganic salts. Fermentation may be carried out in the same manner as in the production of usual antibiotics, for example, a liquid medium, a submerged aerobic condition and the like. The pH of the medium is preferred to be about 5.5 to 8.5. The temperature may be kept at about 20°–40° C., preferrably about 20°–35° C. PLM B and PLM C can be isolated from the fermentation broth by the usual methods for isolating fermentation products. The detail of the production is disclosed in Japanese Patent Application Nos. 1981/99315 and 1981/180628 and U.S. application Ser. No. 432,102 (Tanaka et al.), filed concurrently herewith.

The compounds of this invention have a wide range of anti-microbial spectrum, being effective against both gram-positive and gram-negative bacteria. Furthermore, they strongly inhibit β-lactamases of both penicillinase-type and cephalosporinase-type. Therefore, the compunds are useful as medicaments, veterinary drugs and disinfectants.

The results of antibacterial test and β-lactamase inhibitory test are shown below:

(1) Antibacterial Spectrum

TABLE 2

| Test Microorganism | Minimum Inhibitory Concentration (μg/ml) | | |
|---|---|---|---|
| | Deoxy PLM B | Deoxy PLM C | Dihydro PLM C |
| *Staphylococcus aureus* 209P JC-1 | 3.13 | 0.78 | 12.5 |
| *Streptococcus pneumoniae* I | 1.56 | 0.2 | 3.1 |
| *Escherichia coli* NIHJ JC-2 | 1.56 | 0.78 | 12.5 |
| *Klebsiella pneumoniae* SRL-1 | 0.78 | 0.78 | 25 |
| *Klebsiella* sp. 363(R) | 1.56 | 0.78 | 12.5 |
| *Proteus mirabilis* PR-4 | 0.78 | 0.78 | 25 |
| *Enterobacter cloacae* 233 | 6.25 | 3.13 | >100 |
| *Pseudomonas aeruginosa* ATCC 25619 | >100 | >100 | >100 |

Notes:
Determined by agar dilution method;
Inoculum size is $10^6$ cells/ml;
Cultivation in sensitivity-disc agar at 37° C. overnight.

(2) β-Lactamase inhibitory test

| Source of β-lactamase | Minimum Effective *3 Concentration (μg/ml) | | |
|---|---|---|---|
| | Deoxy PLM B | Deoxy PLM C | Dihydro PLM C |
| *Enterobacter cloacae* 92 *1 | 0.002 | 0.002 | 0.008 |
| *Klebsiella* sp. 363 *2 | 0.063 | 0.125 | 0.004 |

Notes:
*1 producing β-lactamase of cephalosporinase-type
*2 producing β-lactamase of penicillinase-type
*3 The test compound was incubated with enzyme at room temperature for 10 minutes prior to adding an indicator and the minimum concentration to inhibit color change was determined.

Accordingly, the compounds of this invention may be orally or parenterally administered to human or animals. They may be formed to tablets, capsules, powder and the like in admixture with diluents, stabilizing agents, preservatives, wetting agents, detergents and the like for oral administration. They can also be parenterally administered in the form of, for example, injection, ointment and suppository. The dosage of these antibiotics is generally about 1/10 times to several times of cefalotin though it depends on the purpose of treatment. For example, the daily dosage to a human adult is about 0.1 to about 10 g in subcutaneous injection. The compounds can synergistically increase the antimicrobial activity of β-lactam antibiotics against β-lactamase-producing bacteria because of the β-lactamase inhibitory activity. Therefore, the compounds may be used with known β-lactam antibiotics such as penicillins (e.g. benzylpenicillin, phenoxymethylpenicillin, carbenicillin, ampicillin, amoxycillin and the like) and cephalosporins (e.g. cefaloridine, cefalotin, cefazorin, cefalexin, cefoxitin, cefacetrile, cefamandole, cefapirin, cefradine, cefaloglycin, ceftezol, cefatrizine, cefmetazol and the like).

The following examples are given solely for the purpose of illustration and are not to be construed as limitation of the present invention.

EXAMPLE 1

Anhydrous titanium trichloride (17.6 mg, 5.0 eq. moles) was dissolved in distilled water (20 ml) deaired under reduced pressure. The solution was stirred in nitrogen atmosphere and adjusted to pH 7.0 with 1N sodium hydroxide to give a balck suspension. A solution of PLM B (11 mg) in distilled water (1.5 ml) deaired under reduced pressure was added thereto. An additional suspension of anhydrous titanium trichloride (8.8 mg, 2.5 eq. moles) prepared in the same manner as noted above was mixed therewith after 1 hour. Air was introduced into the reaction vessel after 13 minutes to oxidize the excess reagent. The resultant white precipitate was removed by centrifugation after adjustment of the reaction mixture to pH 7.0. The supernatant was condensed to 3 ml under reduced pressure below 25° C., applied to a column of Biogel P-2 (250 ml, Bio-Rad Co., Ltd.) and eluted with distilled water. Fractions were checked by high performance liquid chromatography (HPLC). Those containing the reduced product were collected, condensed under reduced pressure below 25° C. and lyophilized to give sodium salt of 3-carboxymethylthio-6-(1-hydroxysulfonyloxyethyl)-7-oxo-1-azabicyclo[3.2.0]-hept-2-ene-2-carboxylic acid as a pale yellowish amorphous powder (8 mg).

EXAMPLE 2

A suspension of anhydrous titanium trichloride (18.6 mg, 5.0 eq. moles) in distilled water (20 ml) was prepared in the same manner as in Example 1 and mixed with a solution of PLM C sodium salt (10 mg) in distilled water (1.5 ml) deaired under reduced pressure. The mixture was stirred for 1.5 hours and air was introduced to the reaction vessel. Pale yellowish amorphous powder (6 mg) of 3-di-hydroxymethylthio-6-(1-hydroxysulfonyloxyethyl)-7-oxo-1-azabicyclo[3.2.0]-hept-2-ene-2-carboxylic acid sodium salt was obtained by following the same procedure as noted in Example 1.

EXAMPLE 3

A solution of PLM C sodium salt (10 mg) in 0.05 M phosphate buffer solution (pH 7.0, 3.8 ml) was mixed with an aqueous solution (264 μl) of sodium borohydride (1.056 mg, 1.15 eq. moles) under stirring at room temperature. Sodium chloride (1 g) was added thereto after 10 minutes. The mixture was passed through a column of Diaion HP-20AG (100–200 mesh, 20 ml, Mitsubishi Kasei Co., & Ltd.) pretreated with a 10% aqueous solution of sodium chloride. The column was eluted with the same solution of sodium chloride to give fractions; each contains 5 ml of eluate. The presence of the reduced product was checked by HPLC and active fraction Nos. 8–16 were collected and condensed to 5 ml under reduced pressure below 25° C. The precipitated sodium chloride was removed by filtration. The filtrate was applied to a column of Sephadex G-10 (40–120μ, 300 ml) which was eluted with water. The eluate was desalted, condensed to about 3 ml under reduced pressure below 25° C. and lyophilized to give a colorless amorphous powder (8 mg) of 3-hydroxymethylsulfinyl-6-(1-hydroxy-sulfonyloxyethyl)-7-oxo-1-azabicyclo[3.2.0]-hept-2-ene-2-carboxylic acid sodium salt.

What we claim is:

1. A compound of the formula:

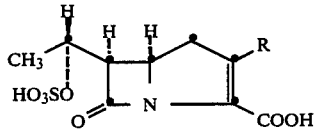

wherein R is, dihydroxymethylthio, formylthio or hydroxymethylsulfinyl or a pharmaceutically acceptable salt thereof.

2. A compound claimed in claim 1 wherein R is dihydroxy-methylthio or formylthio.

3. A compound claimed in claim 1 wherein R is hydroxy-methylsulfinyl.

* * * * *